United States Patent [19]
Ledford, Jr. et al.

[11] Patent Number: 6,007,602
[45] Date of Patent: Dec. 28, 1999

[54] APPARATUS AND METHOD FOR CHEMICAL MODULATION

[75] Inventors: Edward B. Ledford, Jr., Lincoln, Nebr.; John B. Phillips, Carbondale, Ill.

[73] Assignee: Board of Trustees of Southern Illinois University on Behalf of Southern Illinois University at Carbondale, Carbondale, Ill.

[21] Appl. No.: 09/051,535
[22] PCT Filed: Oct. 10, 1996
[86] PCT No.: PCT/US96/16376
§ 371 Date: Jun. 12, 1998
§ 102(e) Date: Jun. 12, 1998
[87] PCT Pub. No.: WO97/13570
PCT Pub. Date: Apr. 17, 1997

Related U.S. Application Data
[60] Provisional application No. 60/005,147, Oct. 13, 1995.

[51] Int. Cl.[6] .................................................. B01D 15/08
[52] U.S. Cl. ..................... 95/8; 95/86; 95/87; 96/102; 96/104; 96/105; 210/656; 210/198.2
[58] Field of Search ................... 95/8, 86, 87; 96/102, 96/104, 105; 210/656, 198.2

[56] References Cited

U.S. PATENT DOCUMENTS

| | | | |
|---|---|---|---|
| 3,043,127 | 7/1962 | Ford | 95/87 |
| 3,057,183 | 10/1962 | Ford | 96/102 |
| 5,135,549 | 8/1992 | Phillips | 95/8 |
| 5,196,039 | 3/1993 | Phillips | 210/656 |

*Primary Examiner*—Ernest G. Therkorn
*Attorney, Agent, or Firm*—Kilyk & Bowersox, P.L.L.C.

[57] ABSTRACT

An apparatus and a method are described for forming a chemical modulation of a substance present in a fluid stream, which utilize a movable device, such as a movable heater, to induce changes in the retention of a chemical substance flowing through the modulator tube. The modulator tube has an inlet, a first portion in communication with the inlet, a second portion in communication with said first portion, and an outlet in communication with said second portion. The method involves causing a chemical modulation by moving retention alteration device relative to a modulator tube.

20 Claims, 1 Drawing Sheet

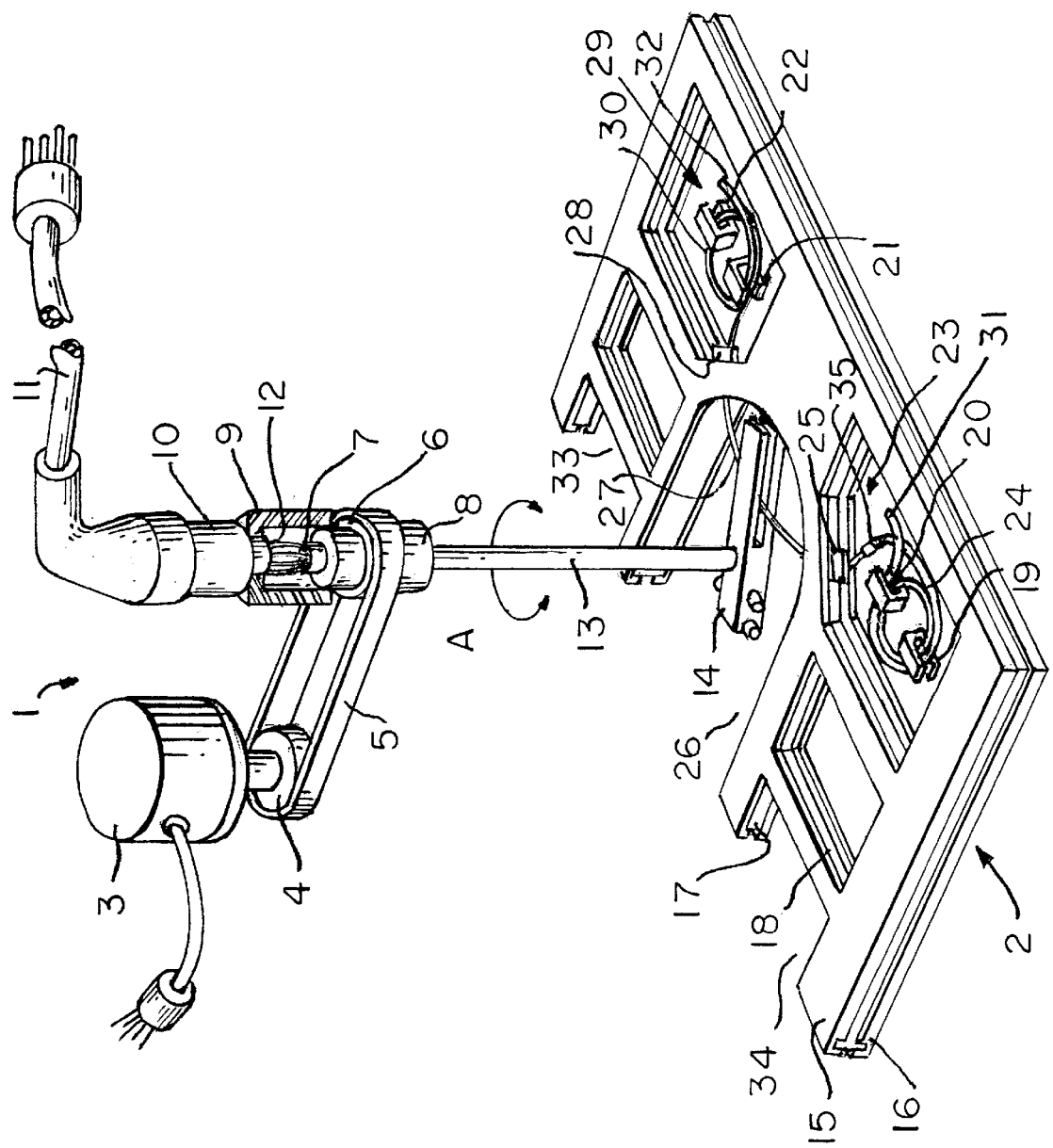

6,007,602

APPARATUS AND METHOD FOR CHEMICAL MODULATION

REFERENCE TO RELATED APPLICATIONS

This application is a 371 of PCT/US96/16376 filed Oct. 10, 1996 and claims the benefit of U.S. provisional application No. 60/005,147, filed Oct. 13, 1995.

FIELD OF THE INVENTION

The present invention relates to the field of chemical separation, particularly gas chromatography.

BACKGROUND OF THE INVENTION

Prior art devices have used moving retention alteration means, such as a moving heater, to form a chemical substance into a single chemical pulse within a tube. Such apparatus is described by DeFord in U.S. Pat. Nos. 3,043, 127 and 3,057,183. Many devices employing moving members for injecting substances onto chromatographic columns are known. All such devices form chemical substances into substantially a single chemical pulse so long as deleterious chromatographic practices resulting in accidental peak splitting are avoided. These prior art devices suffer a disadvantage in that a substance is formed only into a single chemical pulse in a tube.

Another class of prior art devices is the comprehensive multidimensional gas chromatograph of Phillips and Liu. described in U.S. Pat. Nos. 5,196,039 and 5,135,549. These devices suffer a disadvantage in that resistive heaters used to form substances into multiple chemical pulses in a tube have shown a tendency to burn out in practice, and to present difficulties with manufacture.

The present invention solves the aforementioned problems.

SUMMARY OF THE INVENTION

It is an object of this invention to provide a method of chemical modulation.

It is an object of this invention :o provide an apparatus for chemical modulation.

It is an object of this invention to improve the reliability of multidimensional gas chromatographs.

It is an object of this invention to establish a technical basis for miniaturizing a comprehensive multidimensional gas chromatograph.

It is an object of this invention to simplify the use of a comprehensive multidimensional gas chromatograph.

It is an object of this invention to provide a dimensional gas chromatograph comprising a cartridge structure.

In accordance with these and other purposes of the invention, a method of chemical modulation is provided whereby a retention alteration means is moved relative to a modulator tube.

Furthermore, apparatus is provided, comprising a retention alteration means, moving means, and a modulator tube, said apparatus providing a chemical modulation.

The present invention will be better understood with reference to several terms, exemplary non-limiting definitions of which, in the context of this application, are set forth below:

A "column" is a device for containing a fluid stream and which provides a chemical separation of retainable substances, e.g., a gas chromatographic column or a capillary electrophoresis tube or other tube.

"Fluid stream" is a directional transport of a gas, liquid, or supercritical fluid. A fluid stream through a chemical separation column has a flow which is considered to move in a downstream direction. An "Upstream" direction is a direction against the fluid stream flow direction.

"Tube" represents a device such as a channel capable of carrying a fluid stream. A tube may have an arbitrary cross section. A rectangular channel etched into the surface of a silicone wafer would be a "tube" in this context. A tube could also comprise multiple separate lengths of tubing or column linked together to form a single tube.

"Chemical flux" is the number of molecules of a substance passing through a cross section of a tube in a given time interval. Its units are area/time, in accordance with the general scientific meaning of the term flux. It is clear that the flux of a substance in a flowing stream may vary with time, and that a graph of such variation could be treated as a time-domain signal. It is also clear that if the concentration of chemical substance varies as a function of position within a tube, the flux would also vary as a function of the position of the cross section To which flux is referred. Hence, flux may vary with position in a tube. Flow velocity couples temporal and positional dependencies of a flux.

"Chemical pulse" is a variation of a chemical flux having a single maximum in time or position.

"Chemical modulation" is a method of transforming a flux of a substance flowing in a stream into at least two chemical pulses.

It will be appreciated that a time-domain signal representing the flux of substance has a Fourier spectrum, so we may refer to the Fourier spectrum of a chemical flux. Chemical modulation, as distinct from simple focusing, may introduce a substantial discontinuity into the Fourier spectrum of a chemical flux.

"Retention" is an ability of a tube to retard a chemical substance in the presence of a carrier fluid stream. For example, chilling a metal tube sustaining a flow of humidified air may retard the flow of water relative to air through the formation of condensation or ice on the inner wall of the tube. In chromatographic apparatus, substances are commonly retarded relative to a carrier flow by means of chemical interaction with a stationary phase.

"Retention alteration means" is a means of altering, within a region of a tube, the retention of a chemical substance. For example, the oven of a gas chromatograph, the moving heater of chromatothermographic art, and cold traps are each examples of retention alteration means which alter retention by means of temperature. An electric field can retard electrically charged substances relative to a carrier flow, as in modulated ion mobility spectroscopy. Thus an electric field can be used as a retention alteration means.

"Modulator tube" is a tube having an inlet, a first portion in communication with the inlet, a second portion in communication with said first portion, and an cutlet in communication with said second portion. Chemical modulation occurs within the modulator tube. The first and second portions may be continuous with one another but lie on opposite sides of a centrally located region of the length of the tube effected by a retention alteration means during operation.

"Moving" means causing a mechanical advancement of retention alteration means along a tube. For example, rotation of a mirror, could cause a laser beam to move along a tube. Mechanical displacement of a heater along a chromatographic tube, as in chromatothermographic art, is an example of "moving" in the context of this patent specification.

"Accumulation" means collecting and holding retainable substances in an accumulation portion of a modulator tube.

"Focusing action" is a process of transferring retainable substances from an accumulation portion of a modulator tube to a focusing portion thereof, such that the length of modulator tube occupied by a chemical substance in the focusing portion is less than the length of modulator tube occupied by a chemical substance in the accumulation portion. The focusing process generates a substantial gap or space between a chemical pulse and additional modulated substance, if any, again accumulating in the accumulation portion of the modulator tube. Thus the rear of one chemical pulse and the front of the next are formed by one focusing action, and each focusing action results in one chemical pulse.

"Focusing cycle" means one occurrence of a focusing action.

"Acceleration" is a process of increasing the velocity of a chemical pulse as it moves along an acceleration portion of a modulator tube. Acceleration operates through a change in retention of a modulatable substance.

Accumulation, focusing and acceleration "portions" means regions of a modulator tube in which accumulation, focusing and acceleration, respectively, take place.

"Cartridge structure" means a cartridge type housing for a chromatographic column rigid enough to transmit biasing force from a biasing means to a ferrule, thereby causing the ferrule to seal around a chromatographic column. A cartridge structure eliminates the need for threaded gas connection fittings commonly employed in gas chromatographic art.

"Detector" means apparatus having an inlet, and which transduces a chemical flux to time-domain electrical signal. By "inlet" we mean not only the port through which a substance enters a detector proper, but also a transfer line necessary for the function of the detector. For example, mass spectrometer detectors commonly employ transfer lines. The input end of the transfer line would be considered the detector inlet in the present context Additional terms and explanations which further detail the art of thermal modulation and multidimensional chemical separation may be found in U.S. Pat. Nos. 5,196,039 and 5,135,549, which are incorporated in their entireties herein, particularly the relevant portions of those patents which discuss thermal modulation of a substance peak and the formation of multiple chemical pulses from such a peak.

According to the foregoing definitions, the present invention provides a method of causing a chemical modulation comprising moving a retention alteration means relative to a modulator tube. Furthermore, the present invention provides apparatus comprising a retention alteration means, moving means, and a modulator tube, said apparatus providing a chemical modulation.

BRIEF DESCRIPTION OF THE DRAWINGS

The present invention will be better understood with reference to the accompanying drawing, which represents a retrofit kit for a common laboratory gas chromatograph.

DETAILED DESCRIPTIONS OF THE PREFERRED EMBODIMENTS

With reference to the drawing Figure, an exemplary embodiment of the present invention is provided and includes a drive assembly 1 and a column cartridge 2. The drive assembly consists of a stepper motor 3, a sprocket pulley 4, a timing belt 5, a sprocket pulley 6, an upper bearing 7, a lower bearing 8, a coupling 9, a slip ring assembly 10, an electrical connection to the slip ring assembly 11, electrical leads 12, machinable ceramic shaft 13, and a slotted heater subassembly 14.

The column cartridge assembly consists of upper shell 15, a lower shell 16, an insulation layer 17, a diecut kapton film 18 bearing slitted tabs 19, 20, 21 and 22, a first column chamber 23, a first column 24 mounted within the first column chamber in a substantially planer coil anchored by the slitted tabs, a thermally conducting metal tab 25, a modulation zone 26, a modulator tube 27, a thermally conducting metal tab 28, a second column chamber 29, and a second column 30 mounted similarly to the first column. The first column has an inlet end 31, shown unconnected in the diagram. The second column has an outlet end 32, shown unconnected in the diagram. The column cartridge also provides a detector interface zone 33, and an injector interface zone 34. Not appearing in the diagram are mounting plates, spacer posts, brackets and the like matters of common mechanical art used to maintain the various components in the relative positions indicated.

In operation, the inlet end of the fist column is connected to an injector, and the outlet end of the second column is connected to a detector. The specific connection means may vary depending on the type of instrument with which the present invention is employed. For example, if used as a retrofit kit for the Hewlett Packard 5890 gas chromatograph, the column cartridge assembly is mounted in the gas chromatograph oven, and the column ends are connected using standard methods known in the gas chromatographic art. In this case, the drive assembly is mounted on top of the gas chromatograph oven, and the ceramic shaft is fed through the top of the oven wall. The slotted heater permits the column cartridge to be inserted or removed from the gas chromatograph oven with ease.

The column cartridge can be used in a gas chromatograph of novel construction wherein chambers 23 and 29 function as miniature oven spaces. This use of the cartridge structure is facilitated by incorporating column connection means into the cartridge itself. In common chromatographic art, columns are connected to gas chromatographs by threaded fittings which, when twisted, supply the mechanical bias needed to compress ferrules. The cartridge structure of the present invention eliminates the need for threaded fittings, i.e., bayonet connections may be used instead. One or more bayonet connections can be provided at the inlet and/or outlet end of either or both columns. With respect to gas connections to the columns proper, the cartridge structure is mechanically rigid enough to transmit mechanical force from a spring biasing means, any number of such biasing means being commercially available. By equipping the cartridge structure with graphite ferrules mounted in the interface zones 33 and 34, and providing mating bulkheads in an instrument chassis (not shown in FIG. 1), the cartridge structure can transmit bias force sufficient to cause such ferrules to seal around the inlet and outlet ends of the columns, the latter being guided from the column chambers to the interface zones with appropriate care to avoid cold spots in intervening insulation layers separating the various cartridge chambers shown in FIG. 1. These measures result in a plug-in column cartridge. An example of one type of bayonet connection is the glass press-fit connector indicated at 35 connecting the outlet of the first column to the inlet portion of the modulator tube.

In operation, sample substance traversing the first column enters the modulation chamber through a metal tab which prevents formation of cold spot in the thermal insulation barrier between the first column chamber and the modulation zone. In the modulation zone, the column is bent into an arc. To perform a focusing action, the slotted heater, actuated by the stepper motor, belt and sprocket assembly (available from Berg, Inc., East Rockaway, N.Y.), is scanned over the modulator tube in an upstream to downstream direction. The temperature of the entire slotted region of The heater is preferably maintained at a high enough value that retention of a sample substance within the modulator tube is substantially reduced in the local region of the tube to which the slotted heater supplies heat. Sample substance is thereby caused to travel through the locally heated region of the modulator tube at a velocity greater than that with which the heated zone itself propagates down the modulator tube in consequence of the rotation of the slotted heater assembly. Sample substance traverses this heated zone, where it encounters a downstream region of tubing not yet heated because the slotted heater has not yet been rotated over it. Retention in this unheated region is high, and the sample substance is retarded therein. As the heater scans along the modulator tube, substances released by the heated zone build up into a chemical pulse just downstream of the leading edge of the heated zone, resulting in a focusing action. Once the slotted heater reaches the position shown in the diagram, the exposed upstream region of modulator tube is cool, and begins accumulating more chemical substance in preparation for another pass of the slotted heater. When the slotted heater scans over the downstream portions of the modulator tube, the chemical pulse is accelerated out of the modulator tube.

Acceleration occurs because a downstream portion of the modulator tube much longer than the length of the chemical pulse is suddenly heated as the slotted heater is rotated over it. According to a preferred embodiment of the invention, this effect can be facilitated by curvature of the modulator tube, as is shown in the Figure. By manipulating the temperature in different portions of the modulator tube (e.g., setting, assigning, programming or positioning the temperature), the accumulation and focusing of chemical substance, and the accelerating of a chemical pulse, can be achieved. One method of manipulating the temperature as such involves rotating a heater as shown in the Figure, preferably in a unidirectional and smooth downstream directional sweep, although a reciprocating motion could also be used.

From the foregoing discussion, it is apparent that a modulator tube may possess accumulation, focusing and acceleration portions.

To form a second chemical pulse, the slotted heater is again swept over the modulator tube. The slotted heater may preferably be swept unidirectionally so that it circles around for another pass at the modulator tube. Alternatively the slotted heater may be reciprocated about the axis of the ceramic shaft. Either of these types of motion is indicated at A in FIG. 1.

The slotted heater comprises a thermally insulated aluminum heating block. The assembly contains a platinum resistance sensor for temperature control. Common commercially available temperature controllers can regulate the temperature of the slotted heater. Electrical leads of heaters and the temperature sensor are spot welded to stainless steel contacts within the assembly in a suitable manner well known to those skilled in the art.

Electrical leads are fed to the slotted heater through the machined ceramic shaft, the upper end of which is terminated in a slip ring assembly (available from Mercotac, Inc., Carlsbad, Calif.) which provides rotating electrical feedthrough.

In a capillary gas chromatograph the modulator tube can be a length of capillary tubing. Retention of the modulator tube is generally much greater than that of any downstream analytical column, such as the secondary column of a two-dimensional gas chromatograph. This greater retention can be achieved by operating the modulation zone at a lower ambient temperature than a second column. Alternatively, the stationary phase inside the modulator tube can be made much thicker than that of the second column. In the latter construction, it is important to be sure the thick stationary phase does not extend beyond the heated region of the modulator tube, or severe broadening of a chemical pulse may occur.

According to yet another embodiment of the invention, the heater remains stationary and means are provided for moving the modulator tube relative to the heater. Similar accumulation, focusing and acceleration of a chemical pulse can be achieved according to this embodiment but motorized means to move the modulator tube and a more durable modulator tube would be necessary compared to the embodiment wherein the heater moves. One method of moving the modulator tube would require a forward motor to pull the tube in a fist direction, and a second motor to pull the tube in an opposite second direction back to an original position. Alternatively, the heater and modulator tube may both be moved relative to each other.

The present invention provides a method of chemical modulation comprising the steps of providing a modulator tube, introducing a substance into the modulator tube, passing the modulator tube adjacent a retention alteration means to alter retention of the substance in the modulator tube, and moving the retention alteration means relative to the modulator tube. Depending upon the motion of the retention alteration means, the method can be used to cause an accumulation and focusing action. Moving the retention alteration means downstream relative to the flow of substance through the modulator tube causes a focusing action. The intersection or communication between the first and second portions of the modulator tube is defined by a centrally located region of the length of modulator tube having retention therein affected by the retention alteration means.

The first portion of the modulator tube can comprise an upstream portion of a length of tube or column which is independent of any chromatographic column. Upstream in this context meaning upstream of the centrally located communication between the first and second portions of the modulator tube. The tube or column has retention characteristics regardless of how strong or weak. The first portion may instead or additionally comprise a chromatographic column.

The second portion of the modulator tube may comprise a downstream portion of a length of tube or column which is independent of a chemical separator, e.g., chromatographic column. Downstream in this context meaning downstream of the centrally located intersection or communication between the first and second portions of the modulator tube.

The method of the present invention may further comprise connecting the inlet of the modulator tube to an outlet of a chemical separation column, particularly a chromatographic column. The outlet of the modulator tube may also or instead be connected to the inlet of a chromatographic column. According to a preferred embodiment of the invention for multi-dimensional chemical separation, both the first and second portions are connected to respective chemical separation columns, e.g., gas chromatographic columns.

According to another preferred embodiment of the invention, the first and second columns have different retention mechanisms. For example, the first column may separate a substance introduced therein by volatility, using heat as a retention alteration means, as in temperature programmed operation common in the art. The second column separates the substance which has passed through the first column in a different manner, e.g., by polarity, or by entropic effects associated with temperature stepping, or by activity coefficient. Alternatively, the first column may separate a substance based on both volatility and polarity, and the second column may separate only by volatility. Separation on the first column may proceed on the basis of sample vapor pressure, while the second column may separate on the basis of activity coefficients.

According to another embodiment of the invention, the inlet of the modulator tube is connected to the downstream end of a separation column, and the outlet of the modulator tube is connected directly to the inlet of a detector. The modulator tube provides a final focusing of substance which can increase sensitivity of the detector to that substance many fold.

When the modulator tube of the present invention moves relative to and passes adjacent the retention alteration means, the moving results in accumulation of substance within the first portion of the modulator tube, focusing action upon the substance so as to form a chemical pulse thereof, and acceleration of the chemical pulse. Providing a curvature in the modulator tube as shown in the Figure can be advantageously utilized to further enhance the accumulating, focusing and accelerating actions.

The present invention employs a mechanical movement to form a chemical substance into not just a single chemical pulse, as has been done in the prior art, but into a chemical modulation comprising two or more chemical pulses. The described method and apparatus for chemical modulation produce surprising results, some of which are described as follows:

The present invention is more reliable than modulation methods previously known, and is commercially viable. The invention, by virtue of the cartridge structure, makes column changes far less laborious than is common in present day chromatographic practice. The invention creates a technical basis for miniaturizing multidimensional gas chromatographs. The present invention can enhance detection sensitivity in gas chromatography by an order of magnitude.

EXAMPLE

The present invention will be better understood by considering the following example of a typical operation.

A mixture of several substances is injected into a first chromatographic column. Over a period of a few minutes, the mixture is resolved into some number of chromatographic peaks, which number may be smaller than the number of substances, meaning that two or more substances may coelute within one of the aforementioned chromatographic peaks. Each chromatographic peak elutes from the first chromatographic column having a baseline width of typically ten seconds. The modulation cycle may be operated every two seconds. As each ten second wide chromatographic peak traverses the modulator tube, it is cut into five chemical pulses by the modulator, each pulse forming two seconds after the previous pulse has formed. Due to focusing, the pulses themselves are typically very much narrower than the time interval separating them. A typical pulse width would be 26 milliseconds at baseline near the outlet portion of the modulator tube.

Although the present invention has been described in connection with preferred embodiments, it will be appreciated by those of skill in the art that additions, modifications, substitutions and deletions not specifically described may be made without departing from the spirit and scope of the invention defined in the appended claims.

We claim:

1. A method of thermal modulation for generating chemical pulses in a fluid stream flowing through a modulator tube, said tube comprising an inlet, a first portion which is a length of said tube, a second portion which is a length of said tube in communication with said first portion, and an outlet portion, said method comprising the steps of:

(A) creating a fluid stream in a direction through said tube to produce a carrier fluid stream;

(B) introducing a sample into the carrier fluid stream, said sample comprising one or more sample substances;

(C) manipulating the temperature of the first portion to cause at least a portion of the sample to be retained therein;

(D) manipulating the temperature of the second portion such that sample will be retained therein;

(E) accumulating a sample substances in the first portion for a period of time to form a first concentration of sample, the accumulated sample substances being carried into the first portion by the carrier fluid stream;

(F) manipulating the temperature of the first portion to release the first concentration into the carrier fluid stream in the form of a first chemical pulse;

(G) causing the first chemical pulse to be carried in the direction of carrier fluid stream flow toward the second portion;

(H) accumulating the first chemical pulse in said outlet portion so as to focus and hold the first chemical pulse therein for a period of time and form a second concentration of sample which is more compact in distance than the first chemical pulse, sample substances of the first chemical pulse being carried to the outlet portion by the carrier fluid stream;

(I) manipulating the temperature of the first portion to accumulate more sample substances therein for a period of time, the sample substances being carried into the first portion by the carrier fluid stream;

(J) manipulating the temperature of the second portion so as to release the second concentration into the carrier flow stream in the form of an outlet chemical pulse, the outlet chemical pulse being of shorter duration than the first chemical pulse; and (K) manipulating the temperature of the second portion such that a subsequent chemical pulse is retained therein; wherein steps (C), (D), (F), (I), (J) and (K) comprise moving at least one of a retention alteration means and the modulator tube relative to the other to alter retention of substance within the modulator tube.

2. A method according to claim 1, wherein steps (C), (D), (F), (I), (J) and (K) comprise moving the retention alteration means in the direction of flow of the carrier fluid stream.

3. A method according to claim 1, wherein steps (C), (D), (F), (I), (J) and (K) comprise moving at least one of the retention alteration means and the modulator tube relative to the other to alter retention of substance within the modulator tube at and proximal to the communication between the first and second portions, thereby forming the first and subsequent chemical pulses from portions of said sample.

4. A method according to claim 1, further including the steps of providing a detector having a detector inlet, and connecting the modulator tube outlet portion to the detector inlet.

5. A method according to claim 1, wherein steps (C), (D), (F), (I), (J) and (K) comprise moving at least one of a heater and the modulator tube relative to the other to alter retention of substance within the modulator tube.

6. A method according to claim 1, wherein the retention alteration means is a heater having a guide slot, and the modulator tube passes through the guide slot during relative movement between the heater and the modulator tube.

7. A method according to claim 1, wherein the retention alteration means at least partially rotates about an axis of rotation and relative movement between the retention alteration means and the modulator tube comprises at least partially rotating the retention alteration means about said axis.

8. A method according to claim 7, wherein the retention alteration means rotates completely about said axis of rotation in a smooth sweep at a constant speed of rotation.

9. A method according to claim 8, wherein said retention alteration means is connected to a shaft which turns about said axis of rotation at a constant speed of rotation.

10. A method according to claim 1, wherein said steps (H), (I), (J) and (K) are conducted sequentially in that order.

11. A method according to claim 1, wherein said steps (A), (B), (C), (D), (E), (F), (G), (H), (I), (J) and (K) are conducted sequentially in that order.

12. A method according to claim 1, wherein step (J) comprises accelerating the second concentration so that the outlet chemical pulse exits the outlet portion at substantially the same velocity as the velocity of the carrier gas at the outlet portion.

13. A method according to claim 1, wherein said outlet portion has a stationary phase on the inside thereof and step (J) comprises releasing the second concentration into the carrier flow stream to render the outlet chemical pulse substantially unretained on said stationary phase at said outlet portion.

14. An thermal modulation apparatus for generating chemical pulses in a fluid stream flowing through a modulator tube, said apparatus comprising:

a modulator tube having an inlet, a first portion which is a length of said tube in communication with said inlet, a second portion which is a length of said tube in communication with said first portion, and an outlet portion in communication with said second portion;

means for creating a fluid stream in a direction through said tube to produce a carrier fluid stream;

means for introducing a sample comprising one or more sample substances into the carrier fluid stream;

means for manipulating the temperature of the first portion to cause at least a portion of the sample to be retained therein;

means for manipulating the temperature of the second portion such that sample will be retained therein;

means for accumulating a sample substances in the first portion for a period of time to form a first concentration of sample, the accumulated sample substances being carried into the first portion by the carrier fluid stream;

means for manipulating the temperature of the first portion to release the first concentration into the carrier fluid stream in the form of a first chemical pulse;

means for causing the first chemical pulse to be carried in the direction of carrier fluid stream flow toward the second portion;

means for accumulating the first chemical pulse in said outlet portion so as to focus and hold the first chemical pulse therein for a period of time and form a second concentration of sample which is more compact in distance than the first chemical pulse, sample substances of the first chemical pulse being carried to the outlet portion by the carrier fluid stream;

means for manipulating the temperature of the first portion to accumulate more sample substances therein for a period of time, the sample substances being carried into the first portion by the carrier fluid stream;

means for manipulating the temperature of the second portion so as to release the second concentration into the carrier flow stream in the form of an outlet chemical pulse, the outlet chemical pulse being of shorter duration than the first chemical pulse; and means for manipulating the temperature of the second portion such that a subsequent chemical pulse is retained therein.

15. An apparatus according to claim 14, wherein said means for manipulating the temperature of the first portion to release the first concentration into the carrier fluid stream comprises a retention alteration means.

16. An apparatus according to claim 14, wherein said means for manipulating the temperature of the first portion to release the first concentration into the carrier fluid stream comprises a moving retention alteration means.

17. An apparatus according to claim 14, wherein said means for manipulating the temperature of the first portion to release the first concentration into the carrier fluid stream comprises a moving heater.

18. An apparatus according to claim 14, wherein said means for manipulating the temperature of the second portion to release the second concentration into the carrier fluid stream comprises a retention alteration means.

19. An apparatus according to claim 14, wherein said means for manipulating the temperature of the second portion to release the second concentration into the carrier fluid stream comprises a moving retention alteration means.

20. An apparatus according to claim 14, wherein said means for manipulating the temperature of the second portion to release the second concentration into the carrier fluid stream comprises a moving heater.

* * * * *